United States Patent [19]

Nagashima

[11] Patent Number: 5,141,722
[45] Date of Patent: Aug. 25, 1992

[54] DEODORIZING AND STERILIZING APPARATUS

[75] Inventor: Yasuaki Nagashima, Konan, Japan

[73] Assignee: Zexel Corporation, Tokyo, Japan

[21] Appl. No.: 695,082

[22] Filed: May 3, 1991

[30] Foreign Application Priority Data

May 9, 1990 [JP] Japan .................. 2-119243

[51] Int. Cl.$^5$ .......................... A61L 2/00
[52] U.S. Cl. .................... 422/292; 422/28; 422/29; 422/30; 422/37; 422/305; 422/306; 422/186.07
[58] Field of Search .................. 422/28, 29, 30, 32, 422/37, 292, 298, 305, 306, 186, 186.07, 186.10

[56] References Cited

U.S. PATENT DOCUMENTS

| | | | |
|---|---|---|---|
| 4,029,578 | 6/1977 | Turk | 210/760 |
| 4,035,296 | 7/1977 | Armstrong | 210/194 |
| 4,131,526 | 12/1978 | Moeglich | 204/152 |
| 4,619,733 | 10/1986 | Kooi | 162/37 |
| 4,902,381 | 2/1990 | Meredith | 162/66 |
| 5,053,140 | 10/1991 | Hurst | 422/28 |

Primary Examiner—Robert J. Warden
Assistant Examiner—Laura E. Collins
Attorney, Agent, or Firm—Wenderoth, Lind & Ponack

[57] ABSTRACT

A deodorizing and sterilizing apparatus includes a reaction chamber in which ozone generated by an ozone generator and chlorine dioxide generated by a chlorine dioxide generator react together to form chlorine trioxide and in which the chlorine trioxide is reacted with an article or air to be deodorized and sterilized, thereby deodorizing and sterilizing the article or air. The apparatus also includes an adsorbent for removing ozone and chlorine from a gas after reaction. With this construction, the apparatus is capable of performing an effective deodorizing and sterilizing process even at a low humidity level.

4 Claims, 2 Drawing Sheets

|  | $O_3$ CONCENTRATION | $ClO_2$ CONCENTRATION | RELATIVE HUMIDITY | NUMBER OF LIVE MICROORGANISMS AFTER STERILIZATION |
|---|---|---|---|---|
| $O_3$ | 200 ppm |  | MORE THAN 90% | LESS THAN $10^2$ |
| $ClO_2$ |  | 200~300 ppm | MORE THAN 99% | LESS THAN $10^2$ |
| $ClO_3$ | 100 ppm | 200~300 ppm | MORE THAN 60% | LESS THAN $10^2$ |
| | 100 ppm | 200~300 ppm | MORE THAN 50% | LESS THAN $10^2$ |

DEODORIZING AND STERILIZING APPARATUS

BACKGROUND OF THE INVENTION

1. Field of the Invention

The present invention relates to a deodorizing and sterilizing apparatus using ozone and chlorine dioxide.

2. Description of the Prior Art

Japanese Patent Publication No. 58-25437 discloses a deodorizing and sterilizing method using ozone in which ozone is introduced at a concentration exceeding 100 ppm so as to sterilize and decompose biohazard factors and, thereafter, residual ozone is removed by activated carbon.

According to this method, surface sterilization requires sterilization conditions including an ozone concentration of 200 ppm, a humidity exceeding 90%, and a treatment time of more than 4 hours (according to an article entitled "Fundamental Study on Effectiveness of Ozone Fumigation Disinfection in the Region of Laboratory Animals", August, 1989). This means that the ozone sterilization must be carried out at a very high humidity level exceeding 90%.

Another deodorizing and sterilizing method using ozone is disclosed in Japanese Patent Publication No. 63-59705 in which ozone is added at a concentration of 10 to 5000 ppm and decomposed by being subjected to a catalytic and discharge reaction. This method also requires a very high humidity level exceeding 90% when applied to a surface sterilization of bacteria.

Japanese Patent Publication No. 63-108137 discloses a deodorizing and sterilizing method by using chlorine dioxide adsorbed on a porous material. This method also needs a humidity exceeding 99% as an indispensable condition. As in the case of the foregoing deodorizing and sterilizing methods using ozone, this method using chlorine dioxide has a problem that a very high humidity level is needed.

Another drawback associated with the ozone deodorization and sterilization method is a relatively low permeability to an object to be sterilized. For instance, the permeability to a powdery material such as flour is only about 1 mm. The chlorine dioxide deodorization and sterilization method excels in permeability. However, due to a complicated oxidation mechanism, its sterilizing or bactericidal power is relatively low.

In addition, since the adsorbent and the catalyst have a porous surface structure including a multiplicity of pores of a diameter ranging from several $\mu$ to several Å, when they are used under conditions in which relative humidity exceeds 80%, all the pores are fulled with water molecules. As a consequence, the adsorbability of the adsorbent and the catalytic effect of the catalyst are considerably lowered.

SUMMARY OF THE INVENTION

With the foregoing difficulties in view, it is an object of the present invention to provide a deodorizing and sterilizing apparatus having a sufficient permeability and sterilizing capability in a usual humidity range (40%–60% RH).

According to the present invention, there is provided a deodorizing and sterilizing apparatus which comprises: an ozone generator for generating ozone; a chlorine dioxide generator for generating chlorine dioxide; a reaction chamber for receiving matter (e.g. an article or air) to be deodorized and sterilized, ozone and chlorine dioxide, and for causing the ozone and chlorine dioxide to react together to form chlorine trioxide and subsequently causing chlorine trioxide and said object to react together; and an adsorbent for removing ozone and chlorine from a gas after reaction.

With this construction, ozone and chlorine dioxide react together in the reaction chamber, thereby forming chlorine trioxide. Since chlorine trioxide has a permeability substantially the same as the permeability of chlorine dioxide and a sterilizing capability or power greater than the sterilizing power of ozone, the apparatus is able to provide a sterilizing effect exceeding 99.99% at a relative humidity in the range of from over 50% to over 60%.

The above and other objects, features and advantages of the present invention will become manifest to those versed in the art upon making reference to the detailed description and the accompanying sheets of drawings in which preferred structural embodiments incorporating the principles of the present invention are shown by way of illustrative example.

DETAILED DESCRIPTION

The present invention will be described hereinbelow in greater detail with reference to certain preferred embodiments shown in the accompanying drawings.

Figures 1, 4:
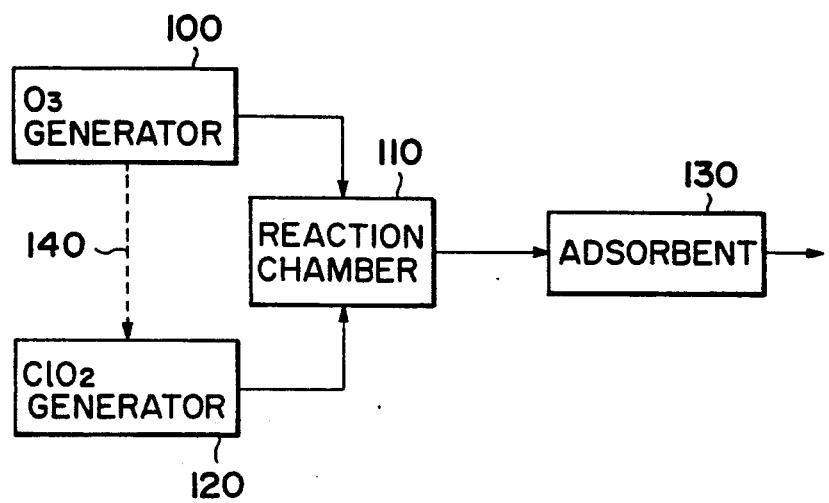
FIG. 1 is a block diagram showing the general construction of a deodorizing and sterilizing apparatus according to the present invention.
FIG. 4 is a comparison table showing data, obtained by experiments, to evidence the sterilizing power of ozone, chlorine dioxide, and chlorine trioxide.

As shown in FIG. 1, a deodorizing and sterilizing apparatus of this invention includes an ozone generator 100 for generating ozone ($O_3$) which in turn is supplied into a reaction chamber 110 into which is also supplied chlorine dioxide ($ClO_2$) generated by a chlorine dioxide generator 120. Ozone reacts with chlorine dioxide to thereby produce chlorine trioxide ($ClO_3$), as indicated by the following chemical reaction expression (1).

$$O_3 + ClO_2 \rightarrow ClO_3 + O_2 \tag{1}$$

Chlorine trioxide ($ClO_3$) then reacts with organic substances contained in or produced from matter (e.g. article or air) to be deodorized and sterilized within the reaction chamber 110 in accordance with the following chemical reaction expression (2), so that a deodorizing and sterilizing process of the matter is performed.

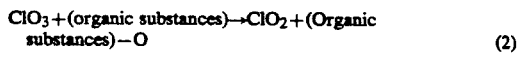
$$ClO_3 + (\text{organic substances}) \rightarrow ClO_2 + (\text{Organic substances}) - O \tag{2}$$

Chlorine which is generated as a result of this reaction, a part of ozone which has not reacted with the organic substances, and other toxic substances are subsequently removed from an exhaust gas through a chemical reaction performed between the gas and an adsorbent 130, in accordance with the following chemical reaction expressions (3) and (4), so that the exhaust gas is rendered clean and nontoxic.

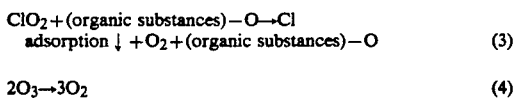

$$ClO_2 + \text{(organic substances)} - O \rightarrow Cl$$
$$\text{adsorption} \downarrow + O_2 + \text{(organic substances)} - O \quad (3)$$

$$2O_3 \rightarrow 3O_2 \quad (4)$$

Chlorine trioxide discussed above is a very unstable substance and when reacted with the organic substances, it immediately separates oxygen in a nascent state and oxidizes the organic substances, thereby deodorizing and sterilizing the matter. The reaction still takes place after chlorine trioxide has penetrated into the matter (such as bacteria in bedding), so that an apparent sterilization efficiency is increased.

A bypass 140 indicated by dash lines in FIG. 1 is provided for circulating ozone through a chlorine dioxide solution. It has been proved by experiments that the bypass 140 is particularly effective to increase the sterilizing effect of the apparatus.

Figure 2:
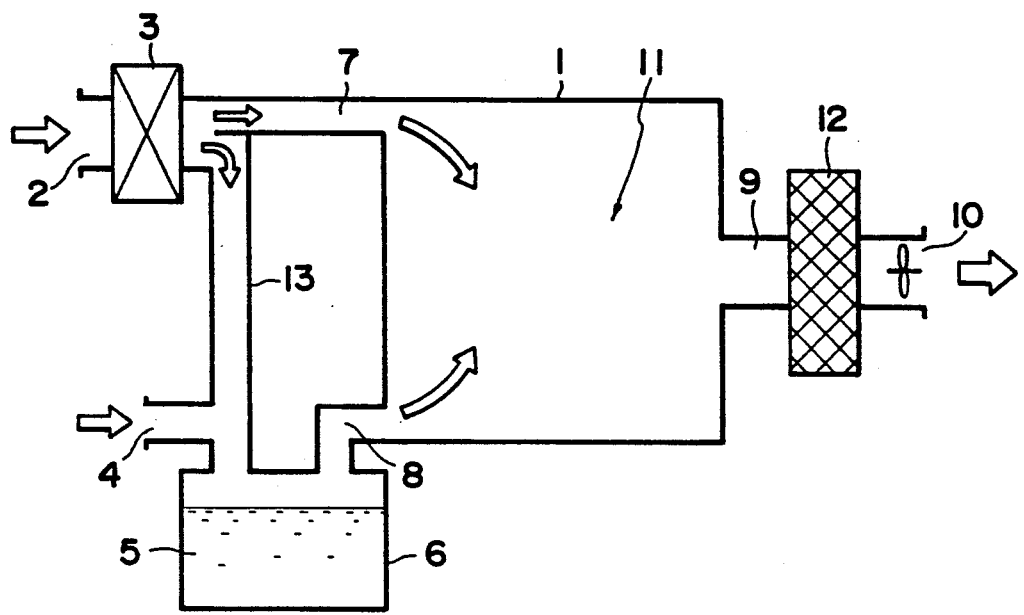
FIG. 2 is a diagrammatical view showing a deodorizing and sterilizing apparatus constructed to process or treat an article, according to the present invention.

FIG. 2 diagrammatically shows a deodorizing and sterilizing apparatus particularly constructed for use with an article (or object).

The apparatus 1 has an air inlet 2, an ozone generator 3 disposed adjacent to the air inlet 2 for converting oxygen ($O_2$) into ozone ($O_3$), a bypass pipe 13 for feeding a part of the ozone from the ozone generator 3 to a chlorine dioxide generation tank 6 containing a chlorine dioxide solution 5, an air intake hole 4 for introducing air into the chlorine dioxide generation tank 6, a deodorizing and sterilizing box 11 for receiving an article or object to be deodorized and sterilized, having an ozone intake hole 7, a chlorine dioxide intake hole 8 and a discharge hole 9, a catalytic layer 12 disposed downstream of the discharge hole 9 and composed of an ozone catalyst and a chlorine adsorbent for adsorbing chlorine and ozone from a gas discharged from the discharge hole 9, and a fan 10 for causing air to flow downstream across the apparatus 1.

Air drawn from the air inlet 2 into the ozone generator 3 is subjected to a silent electric discharge and converted into air containing ozone.

A part of the ozone-containing air is fed directly into the air intake hole 7 and thence to the deodorizing and sterilizing box 11 where the ozone-containing air undergoes a chemical reaction between chlorine dioxide drawn from the chlorine dioxide intake hole 8 in accordance with the chemical reaction expression (1), thereby forming chlorine trioxide.

The remainder of the ozone-containing air flows downstream along the bypass pipe 13 toward the tank 6 and, at a portion of the bypass pipe 13 immediately short of the tank 6, it is mixed with air drawn from the air intake hole 4 and subsequently flows into the tank 6. While the fan 10 is operating, the inside pressure of the tank 6 is lowered due to the suction created in response to the operation of the fan 10, so that chlorine dioxide gas generated from the chlorine dioxide solution 5 in the tank 6 is mixed with an ozone-containing air-and-air mixture. Thus, chlorine dioxide gas is drawn from the chlorine dioxide intake hole 8 into the deodorizing and sterilizing box 11 while being subjected to a chemical reaction between the mixture as indicated by the foregoing chemical reaction expression (1). Subsequently, chlorine dioxide reacts with the ozone-containing air drawn from the ozone intake hole 7 into the deodorizing and sterilizing box 11 to thereby form chlorine trioxide as indicated by the chemical reaction expression (1) mentioned above.

Within the deodorizing and sterilizing box 11, chlorine trioxide oxidizes organic substances contained in the article according to the foregoing chemical reaction expression (2), thus completing a deodorizing and sterilizing operation.

After the reaction, air is caused to flow through the catalytic layer 12 where toxic components are removed by subjecting air to the chemical reactions indicated by the chemical reaction expressions (3) and (4). Finally, air now in a nontoxic state is withdrawn from the apparatus 1 by the fan 10.

Thus, an efficient deodorizing and sterilizing process or treatment of the article or object can be achieved by the apparatus of the foregoing construction.

Figure 3:
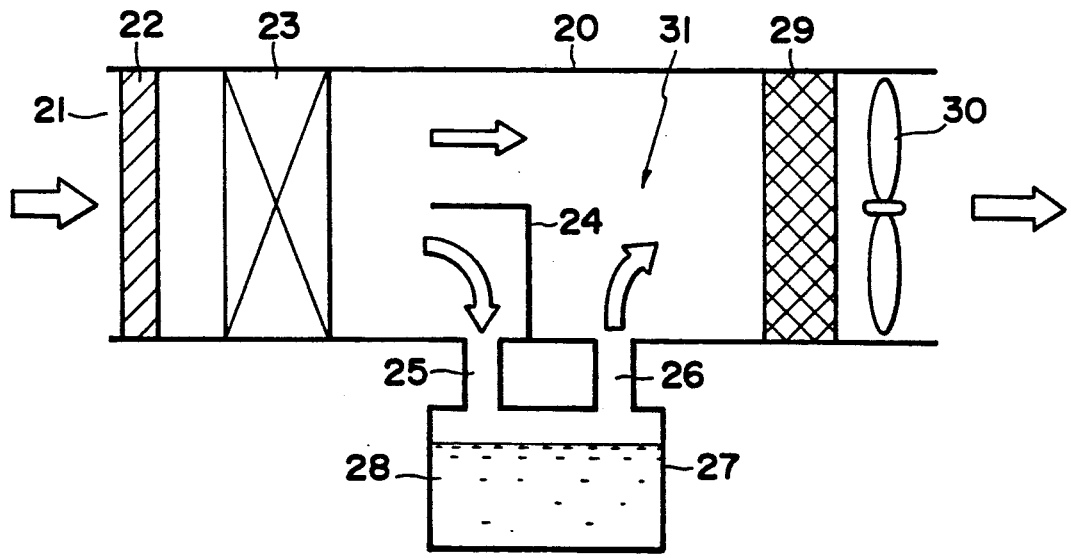
FIG. 3 is a diagrammatical view showing a deodorizing and sterilizing apparatus constructed to process or treat air, according to the present invention.

FIG. 3 diagrammatically shows an apparatus constructed to deodorize and sterilize air according to the present invention.

The deodorizing and sterilizing apparatus 20 includes an air inlet 21, an air filter 22 disposed at the air inlet 21, an ozone generator 23 disposed downstream of the air filter 22, an ozone flow-dividing wall 24, a chlorine dioxide generation tank 27 containing a chlorine dioxide solution 28 and having an intake hole 25 and discharge hole 26, a reaction chamber 31, a catalytic layer 29 disposed downstream of the reaction chamber 31 and composed of a chlorine adsorbent and an ozone catalyst, and a fan 30 for causing air to move through the apparatus 20 as indicated by arrows in FIG. 3.

Air to be treated or processed is drawn by the fan 30 from the air inlet 21 into the deodorizing and sterilizing apparatus 20 in which the filter 22 removes dust and dirt from the air.

The filtrated air flows through the ozone generator 23 in which it is converted into air containing ozone by being subjected to a silent electric discharge process.

The ozone flow-dividing wall 24 is bent into an L shape so that the ozone-containing air is separated by the ozone flow-dividing wall 24 into two parts. A first part of the ozone-containing air is introduced directly into the reaction chamber 31. The remainder or second part of the ozone-containing air is guided into the intake hole 25 and thence to the inside of the tank 27. In the tank 27, the ozone-containing air reacts with chlorine dioxide gas generated from the chlorine dioxide solution 28, thereby forming chlorine trioxide, as indicated by the foregoing chemical reaction expression (1). Air containing chlorine trioxide subsequently flows from the discharge hole 26 into the reaction chamber 31 in which a chemical reaction indicated by the chemical reaction expression (2) takes place to thereby deodorize and sterilize air.

During that time, ozone is fixed on active points on the ozone catalyst of the catalytic layer 29 so that the number of collisions between ozone and chlorine dioxide is increased. Consequently, chlorine trioxide resulting from the reaction between ozone and chlorine dioxide immediately reacts with surrounding organic substances and oxidizes the latter, thereby deodorizing and sterilizing air. At the same time, by the reactions indicated by the chemical reaction expressions (3) and (4), toxic components are removed from air.

Finally, the deodorized and sterilized air is withdrawn from the apparatus 20 by the fan 30.

As described above, according to this invention, the deodorizing and sterilizing process is performed by using chlorine trioxide which is produced by reacting ozone and chlorine dioxide. As appears clear from the table shown in FIG. 4, the conventional sterilizing process using ozone requires a humidity exceeding 90%. In addition, another conventional sterilizing process using chlorine dioxide requires a humidity exceeding 99%. As against these conventional processes, the present invention using chlorine trioxide is able to provide an equivalent sterilizing effect at a humidity more than 60%. With this lower humidity level, the apparatus of this invention is effectively operative without causing appreciable reduction in function of the adsorbent and catalyst when used for the purpose of deodorization and sterilization of air used for air-conditioning.

Obviously, various minor changes and modifications of the present invention are possible in light of the above teaching. It is therefore to be understood that, within the scope of the appended claims, the invention may be practiced other than as specifically described.

What is claimed is:

1. A deodorizing and sterilizing apparatus, comprising:
   (a) an ozone generator for generating ozone;
   (b) a chlorine dioxide generator for generating chlorine dioxide;
   (c) a reaction chamber, operatively connected to said ozone generator and said chlorine dioxide generator, for receiving matter to be deodorized and sterilized, the ozone and the chlorine dioxide, and for causing the ozone and the chlorine dioxide to react together to form chlorine trioxide and subsequently causing the chlorine trioxide and the matter to react together; and
   (d) an adsorbent, operatively mounted to said reaction chamber, for removing ozone and chlorine from a gas after reaction.

2. A deodorizing and sterilizing apparatus according to claim 1, wherein said ozone generator generates ozone through a silent electric discharge in air.

3. A deodorizing and sterilizing apparatus according to claim 1, wherein said chlorine dioxide generator comprises a tank containing therein a chlorine dioxide solution.

4. A deodorizing and sterilizing apparatus according to claim 1, wherein said adsorbent comprises a catalytic layer composed of an ozone catalyst and a chlorine adsorbent.

* * * * *